United States Patent [19]

Luft et al.

[11] Patent Number: 4,906,415

[45] Date of Patent: Mar. 6, 1990

[54] CARRIER-SUPPORTED CATALYST AND PROCESS FOR MAKING MONOCARBOXYLIC ANHYDRIDES

[75] Inventors: Gerhard Luft, Mühltal; Gebhard Ritter, Schutterwald/Baden, both of Fed. Rep. of Germany

[73] Assignee: Hoechst Aktiengesellschaft, Frankfurt, Fed. Rep. of Germany

[21] Appl. No.: 175,745

[22] Filed: Mar. 31, 1988

Related U.S. Application Data

[63] Continuation of Ser. No. 839,725, Mar. 14, 1986, Pat. No. 4,776,987.

[51] Int. Cl.$^4$ .............................................. C07C 51/54
[52] U.S. Cl. .................................... 562/891; 502/155; 502/152; 502/162
[58] Field of Search ................ 260/549; 562/155, 152, 562/162

[56] References Cited

U.S. PATENT DOCUMENTS

| | | | |
|---|---|---|---|
| 4,046,807 | 9/1977 | Kreckertz | 560/549 |
| 4,115,444 | 9/1978 | Rizballa | 560/549 |
| 4,284,585 | 8/1981 | Pugach | 560/549 |
| 4,284,586 | 12/1979 | Pugach et al. | 260/549 |
| 4,559,183 | 12/1985 | Hewlett | 260/546 |

FOREIGN PATENT DOCUMENTS 7176921 10/1982 Japan.

Primary Examiner—Paul J. Killos

[57] ABSTRACT

Monocarboxylic anhydrides of the general formula $(RCO)_2O$ are made by reacting a carboxylic acid ester or dialkylether of the general formulae RCOOR and ROR, respectively, in which R stands for one and the same alkyl radical having from 1-4 carbon atoms, with carbon monoxide in gas phase, in the presence of iodine or bromine or their compounds as a reaction promoter and also in the presence of a carrier-supported catalyst containing noble metal compounds of group VIII of the Periodic System, at temperatures of 130°-400° C. and under pressures of 1-150 bars. To this end, a novel carrier-supported catalyst is used in which the carrier material has a noble metal/chelate-compound formed of the noble metal compound and a chelator containing organonitrogen, organophosphorus, organoarsenic or organosulfur groups applied to it.

16 Claims, No Drawings

CARRIER-SUPPORTED CATALYST AND PROCESS FOR MAKING MONOCARBOXYLIC ANHYDRIDES

CROSS REFERENCE TO RELATED APPLICATIONS

This application is a division of our co-pending application Ser. No. 839,725, filed Mar. 14, 1986, now U.S. Pat. No. 4776987.

This invention relates to a process for making monocarboxylic anhydrides of the general formula $(RCO)_2O$ by reacting a carboxylic acid ester or dialkylether of the following general formulae RCOOR and ROR, respectively, in which R stands for one and the same alkyl group having from 1-4 carbon atoms, with carbon monoxide in gas phase, in the presence of iodine or bromine or their compounds as a reaction promoter and also in the presence of a carrier-supported catalyst containing a noble metal compound selected from group VIII of the Periodic System of the elements, at temperatures at 130°–400° C. and under pressures of 1–150 bars.

Processes of this kind which are carried out in gas phase with the use of a carrier-supported catalyst has already been described in German Specification DE-A 24 50 965 and in Japanese Specification No. 47921/1975. These processes avoid the difficulties normally accompanying operations in liquid phase, e.g. the difficult separation and recycle of suspended and partially dissolved catalyst and, under circumstances, promoter.

The two Specifications describe gas phase processes wherein solid carrier-supported catalysts made by impregnating the carrier material with a dissolved or suspended and even with complex noble metal compounds are used. In this way, it is not possible to fix e.g. an organonitrogen or organophosphorus compound containing trivalent nitrogen or phosphorus in the carrier-supported catalyst; this however has been found generally to affect the catalyst performance and reaction selectivity.

The present invention avoids this deficiency and to this end provides for the catalyst carrier to be impregnated with a noble metal/chelate-compound which has one or more promoters selected from principal group V, e.g. an organylamine or phosphine, already integrated in it.

The invention comprises more particularly using (1) a carrier-supported catalyst in which the carrier has a noble metal/chelate-compound formed of the noble metal compound and a chelator containing organonitrogen, organophosphorus, organoarsenic or organosulfur groups applied to it.

Further preferred and optional features of the invention provide:

(2) for the carrier of the carrier-supported catalyst to have a non noble metal/chelate-compound formed of a non noble metal compound selected from the 6th or 8th subgroup of the Periodic System of the elements and a chelator containing organonitrogen, organophosphorus, organoarsenic or organosulfur groups additionally applied to it;

(3) for the carrier-supported catalyst to contain a non noble metal compound selected from the 1st through 3rd principal groups or the 4th through 6th or 8th subgroups of the Periodic System of the elements as an additional promoter;

(4) for the carrier in the carrier-supported catalyst to have a chelate compound and one of the following chelators:

(a) $Y-(CH_2)_n-Y$ (b) $Y-CH=CH-Y$ (c) $O_2P-CH=CH-PO_2$ (d) $O_2As-CH=CH-AsO_2$ (e) $O_2P-CH_2-CH_2-PO-CH_2-CH_2-PO-CH_2-CH_2-PO_2$ (f) $O_2P-CH_2-CH_2-PO-CH_2-CH_2-PO_2$ (g) 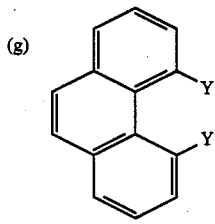

(h) $P(-CH_2CH_2-PO_2)_3$ (i) $R^1-C[-(CH_2)_n-Y]_3$ (j) 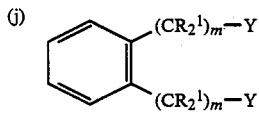

(k) 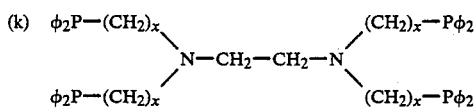

in which
O stands for $C_6H_5-$;
Y stands for $-NR_2^2$, an aryl group containing nitrogen, $-PR_2^2$, $-AsR_2^2$, $-SR^2$ or $-SH$;
$R^1$ stands for $-H$, a $C_1-C_5$-alkyl or $-C_6H_5$;
$R^2$ stands for a $C_1-C_6$-alkyl, a $C_5-C_8$-cycloalkyl or $-C_6H_5$ or $C_6H_5CH_2-$;
n stands for 1 through 6, preferably 1–4;
m stands for 0 through 8, preferably 0–3, and
x stands for 1 or 2
applied to it;

(5) for the carrier-supported catalyst to contain an inorganic oxidic carrier or an active carbon carrier.

(6) for the carrier-supported catalyst to contain altogether 0.01–50 wgt %, preferably 0.1–20 wgt %, chelate compound and non noble metal compound, if desired;

(7) for the carrier-supporting catalyst to be used in the form of particles having a size of 1 through 20 mm.

The invention also relates to the catalyst itself which is used for making monocarboxylic anhydrides by subjecting a suitable ester or ether to a carbonylation reaction and which is characterized in that the carrier has a noble metal/chelate-compound formed of a noble metal belonging to the 8th subgroup of the Periodic System of the elements and a chelator containing organonitrogen, organophosphorus, organoarsenic or organosulfur groups applied to it.

Further preferred and optional features of the carrier-supported catalyst of this invention provide:

(1) for the carrier to have a non noble metal/chelate-compound formed of a non noble metal selected from the 6th or 8th subgroup of the Periodic System of the elements and a chelator containing organonitrogen, organophosphorus, organoarsenic or organosulfur groups additionally applied to it;

(2) for the carrier-supported catalyst to contain a non noble metal compound selected from the 1st through 3rd principal groups or the 4th through 6th or 8th subgroups of the Periodic System of the elements as an additional promoter;

(3) for the carrier to have a chelate compound formed of a metal compound and one of the chelators identified under item (4), (a) through (k) hereinabove applied to it;

(4) for the carrier-supported catalyst to contain an inorganic oxidic carrier or active carbon;

(5) for the carrier-supported catalyst to contain altogether 0.01–50 wgt %, preferably 0.1–20 wgt %, chelate compound and non noble metal compound, if desired.

The catalyst carriers which should preferably be used comprise inorganic oxides, e.g. $SiO_2$, $Al_2O_3$, MgO, $TiO_2$, $La_2O_3$, $ZrO_2$, zeolite, clay, NiO, $Cr_2O_3$, $WO_3$ or corresponding mixed oxides, but also active carbon having a BET-surface area of 1–1000 $m^2/g$, preferably 30–400 $m^2/g$.

The promoters of the 5th or 6th principal group are chemically combined in the chelators used and constitute themselves one of their functional groups encasing the noble metal compounds selected from group VIII, especially Rh, Ir, Pd, or Ru, and also the non noble metal compounds, if any, selected from the 6th or 8th subgroup, especially Cr or Ni, but also W, Fe and Co, like pincers of a crayfish.

One of the advantages of the carrier-supported catalyst and process of this invention resides in the fact that the promoters necessary for increasing the catalyst performance and selectivity and selected from principal group V or VI of the Periodic System of the elements form a functional group Y in the chelators and thus are fixed. It is therefore unnecessary, e.g. for an organonitrogen or organophosphorus promoter to be separated and recycled. The present process for making monocarboxylic anhydrides compares favorably in its higher catalyst performance and selectivity with the prior art methods described hereinabove, which are also carried out in gas phase and with the use of a carrier-supported catalyst.

A further advantage of this invention is seen to reside in the fact that the noble metal/chelate-compounds and optionally non noble metal/chelate-compounds applied to the carrier fail to commence melting at the reaction temperatures necessary for making monocarboxylic anhydrides.

The carrier-supported catalyst and process of this invention are more particularly used for making acetic anhydride from methyl acetate or dimethylether in the presence of methyl iodide or methyl bromide as a reaction promoter. Further suitable promoters are HI, HBr or more generally RI or RBr, where R stands for an alkyl group having 1–4 carbon atoms.

The useful carrier materials have already been specified hereinabove; useful mixed oxides are, e.g. $Cr_2O_3$—$Al_2O_3$, $WO_3$—$Al_2O_3$, MgO—$Al_2O_3$, $SiO_2$—$Al_2O_3$ or $ZrO_2$—$Al_2O_3$. The carrier-supported catalyst should preferably contain 0.01–5 wgt % noble metal and present a particle size of 1 to 20 mm.

The noble metal compounds which should conveniently be used for making the present carrier-supported catalyst, comprise e.g. the following compounds Rhodium:
$RhCl_3$, $RhCl_3.3H_2O$, $RhBr_3$, $RhI_3$, $Rh(NO_3)_3$, $Rh_2(CO)_4Cl_2$, $Rh_2(CO)_4Br_2$, $Rh(CO)_4I_2$, $[P(C_6H_5)_3]_3RhCl$, $[P(C_6H_5)_3]_2Rh(CO)Cl$, $Rh_6(CO)_{16}$, $Rh_4(CO)_{12}$, $Rh_2(O_2CCH_3)_4$, $[RhCl(C_8H_{12})]_2$;

Iridium:
$IrCl_3$, $[Ir(CO)_3Cl]_2$, $Ir[P(C_6H_5)_3]_2(CO)Cl$, $Ir_4(CO)_{12}$, $[IrCl(C_8H_{12})]_2$, $Cl(CO)_2Irpyr$ (pyr=$C_6H_5N$);

Palladium:
$PdCl_2$, $PdBr_2$, $PdI_2$, $(CH_3CO_2)_2Pd[P(C_6H_5)_3]_2$, $PdCl_2[P(C_6H_5)_3]_2$, $Pd(O_2CCH_3)_2$, $PdCl_2(C_8H_{12})$, $(C_6H_5CN)_2PdCl_2$;

Ruthenium:
$RuCl_3$, $Ru_3(CO)_{12}$, $RuCl_2[P(C_6H_5)_3]_3$, $RuCl_2(CO)_2[P(C_6H_5)_3]_2$, $[RuCl_2(CO)_3]_2$.

Useful non noble metal compounds selected from the 6th or 8th subgroup, especially Cr, Ni, but also W, Fe, Co which also undergo reaction with the chelator, comprise e.g. the following:

Chromium:
$Cr(CO)_6$, $CrCl_3$, $C_7H_8Cr(CO)_3$.

Nickel:
$Ni(CO)_4$, $[P(C_6H_5)_3]_2Ni(CO)_2$, $NiCl_2$, $Ni(C_8H_{12})_2$.

The non noble metal compounds selected from the 1st through 3rd principal groups or the 4th through 6th subgroups or 8th subgroup of the Periodic System of the elements, preferably compounds of Li, Na, Mg, Ca, Al, Ti, Zr, V, Cr, W, Fe, Co, Ni are comprised, e.g. of hydroxides, carbonates, carbonyls, hydrides, halides and further salts. It is possible for these non noble metal compounds to be additionally applied to the catalyst carrier, e.g. in the form of a solution by impregnating the carrier therewith.

For making the carrier-supported catalyst of this invention, it is necessary first to have the chelator with the functional groups Y, which is a commercially available product or can be made by methods described in literature. Speaking generally, the chelator is contacted with a solution of one of the noble metal compounds of group VIII and, if desired, one of the non noble metal compounds of the 6th or 8th subgroups with the resultant formation, in known fashion, of chelate compounds having melting points higher than the temperature commonly employed in a carbonylation reaction for making monocarboxylic anhydrides. Next, the carrier material is impregnated with the dissolved conventional chelate compounds to give the finished catalyst. The solvents for the chelate compounds comprise polar and unpolar solvents, e.g. dichloromethane (methylene chloride), chloroform, methanol, benzene, toluene or xylene, in which the carrier material is suspended. Details are indicated in the catalyst description hereinafter.

The quantitative ratio of carboxylic acid ester or dialkylether and iodine (compound) or bromine (compound) in the reaction zone may vary within wide limits. Generally, however, 1 to 500 mols, preferably 1 to 100 mols, carboxylic acid ester and/or dialkylether is used per 1 mol iodine (compound) or bromine (compound). The temperature selected for the reaction zone should be high enough to always have a gaseous reaction mixture therein, irrespective of the conversion rate, and preferably is between 150° and 250° C. The preferred pressure is between 5 and 30 bars.

The reaction mixture should conveniently be contacted with the solid carrier-supported catalyst over a period of from 1 to 1000 seconds, preferably 1 to 180 seconds. The conversion should suitably be effected in a flow tube arranged in upright position, packed with the carrier-supported catalyst or in an autoclave provided with a stirrer or in a shaking autoclave, having the carrier-supported catalyst placed therein. While the carbonylation is generally effected under practically anhydrous conditions, it is allowable for it to be carried out in the presence of minor amounts of water as they are normally found in commercially available starting materials, which however should not exceed 1 mol %, based on the starting materials. In addition, the carbonylation remains substantially uneffected by the presence of minor amounts of methanol in the starting materials or of hydrogen in commercial carbon monoxide.

The reaction mixture coming from the carbonylation zone is gaseous and contains carbon monoxide, methyl iodide, acetic anhydride, unreacted methyl acetate or dimethylether and, under circumstances, minor proportions of acetic acid. The gaseous reaction mixture is cooled with condensation of acetic anhydride, under circumstances, acetic acid. Uncondensed gases, such as CO, $CH_3I$, methyl acetate or dimethylether are recycled to the reaction zone, the reacted ester or ether and CO portions being continously renewed. The anhydrides are easy to separate, i.e. in uncomplicated fashion, by cooling the effluent reaction mixture and recycling the uncondensed gas. This is a particular advantage of the process of this invention. The carrier-supported catalyst is not contaminated; it remains in the reaction zone. As a result, the entire process is rendered considerably simpler.

The following Examples illustrate the invention which is naturally not limited thereto:

EXAMPLES

Autoclave test

A stainless steel (Hastelloy C) autoclave (capacity 0.25 l) provided with a stirrer, various inlets and outlets and a turnable basket receiving the catalyst was used. The carboxylic acid ester or dialkylether was reacted in gas phase with CO-gas in the presence of the agitated solid carrier-supported catalyst. The catalyst was placed in the turnable catalyst basket which also permitted the gases to be mixed. The autoclave was charged with 2.5 ml of a liquid mixture of 20 volume parts methyl iodide and 80 volume parts ester or ether, and heated to the reaction temperature. The carbonylation was started by injecting carbon monoxide. The CO-pressure was maintained constant by continued injection of gas. Details are indicated in the Examples.

EXAMPLE 1

2 ml (1.86 g) methyl acetate, 0.5 ml (1.14 g) methyl iodide and 1.60 g catalyst No. 1 were reacted in the autoclave with carbon monoxide at 180° C. under a CO-pressure of 20 bars. After a reaction period of 1 h, the catalyst performance was found to be 260 g $Ac_2O$ per g Rh per hour. The yield of $Ac_2O$, based on the ester used, was 64% and the selectivity 95%.

EXAMPLE 2

2 ml (1.86 g) methyl acetate, 0.5 ml (1.14 g) methyl iodide and 1.60 g catalyst No. 1 were reacted in the autoclave with carbon monoxide at 175° C. under a CO-pressure of 20 bars. After a reaction period of 1 h, the catalyst performance was found to be 220 g $Ac_2O$ per g Rh per hour. The yield of $Ac_2O$, based on the ester used, was 54% and the selectivity 96%.

EXAMPLE 3

2 ml (1.86 g) methyl acetate, 0.5 ml (1.14 g) methyl iodide and 1.77 g catalyst No. 2 were reacted in the autoclave with carbon monoxide at 166° C. under a CO-pressure of 20 bars. After a reaction period of 1 hour, the catalyst performance was found to be 280 g $Ac_2O$ per g Rh per hour. The yield of $Ac_2O$, based on the ester used, was 64% and the selectivity 97%.

EXAMPLE 4

2 ml (1.86 g) methyl acetate, 0.5 ml (1.14 g) methyl iodide and 1.77 g catalyst No. 2 were reacted in the autoclave with carbon monoxide at 180° C. under a CO-pressure of 20 bars. After a reaction period of 1 hour, the catalyst performance was found to be 380 g $Ac_2O$ per g Rh per hour. The yield of $Ac_2O$, based on the ester used, was 86% and the selectivity 93%.

EXAMPLE 5

2 ml (1.86 g) methyl acetate, 0.5 ml (1.14 g) methyl iodide and 1.78 g catalyst No. 3 were reacted in the autoclave with carbon monoxide at 200° C. under a CO-pressure of 20 bars. After a reaction period of 1 hour, the catalyst performance was found to be 35 g $Ac_2O$ per g Rh per hour. The yield of $Ac_2O$, based on the ester used, was 11.6% and the selectivity 87%.

EXAMPLE 6

2 ml (1.86 g) methyl acetate, 0.5 ml (1.14 g) methyl iodide and 1.70 g catalyst No. 4 were reacted in the autoclave with carbon monoxide at 180° C. under a CO-pressure of 20 bars. After a reaction period of 1 hour, the catalyst performance was found to be 450 g $Ac_2O$ per g Rh per hour. The yield of $Ac_2O$, based on the ester used, was 24% and the selectivity 94.7%.

EXAMPLE 7

2 ml (1.86 g) methyl acetate, 0.5 ml (1.14 g) methyl iodide and 4.4 g catalyst No. 5 were reacted on the autoclave with carbon monoxide at 180° C. under a CO-pressure of 20 bars. After a reaction period of 1 hour, the catalyst performance was 150 g $Ac_2O$ per g Rh per hour. The yield of $Ac_2O$, based on the ester used, was 78% and the selectivity 94%.

EXAMPLE 8

2 ml (1.86 g) methyl acetate, 0.5 ml (1.14 g) methyl iodide and 1.7 g catalyst No. 6 were reacted in the autoclave with carbon monoxide at 180° C. under a CO-pressure of 20 bars. After a reaction period of 1 hour, the catalyst performance was found to be 190 g $Ac_2O$ per g Rh per hour. The yield of $Ac_2O$, based on the ester used, was 45% and the selectivity 93%.

EXAMPLE 9

A steel tube 20 mm wide and 450 mm long was used as a flow tube in upright position and charged with 27.4 g catalyst No. 2 which however contained 0.4 wgt %

Rh. 11 Nl CO (Nl=liter measured at 0° C. under 1.013 bar) and an evaporated mixture (13 ml liquid) of methyl acetate and methyl iodide (molar ratio 11:1) were passed through the flow tube at 172° C. under a pressure of 12.5 bars.

The effluent reaction mixture was cooled to 0° C. at atmospheric pressure and analyzed gas-chromatographically. The space/time-yield was found to be 71 g $Ac_2O$ per liter per hour. The yield of $Ac_2O$, based on the ester used, was 30% and the selectivity 96%.

The carbonylation reaction was effected over a period of 100 hours under these reaction conditions; the performance of the carrier-supported catalyst could not be found to have been reduced.

EXAMPLE 10

2 ml (1.86 g) methyl acetate, 0.5 ml (1.14 g) methyl iodide and 1.7 g catalyst No. 7 were reacted in the autoclave with carbon monoxide at 180° C. under a CO-pressure of 20 bars. After a reaction period of 1 hour, the catalyst performance was found to be 300 g $Ac_2O$ per g Rh.hour. The yield of $Ac_2O$, based on the ester used, was 62% and the selectivity 95%.

EXAMPLE 11

1.86 g dimethylether, 0.5 ml (1.14 g) methyl iodide and 1.7 g catalyst No. 7 were reacted in the autoclave with carbon monoxide at 180° C. under a CO-pressure of 20 bars. After a reaction period of 1 hour, the catalyst performance was found to be 100 g $Ac_2O$ per g Rh per hour. The yield of $Ac_2O$, based on the ether used, was 20.6% and the selectivity 85%.

EXAMPLE 12

2 ml (1.86 g) methyl acetate, 0.5 ml (1.14 g) methyl iodide and 1.7 g catalyst No. 8 were reacted in the autoclave with carbon monoxide at 180° C. under a CO-pressure of 20 bars. After a reaction period of 1 hour, the catalyst performance was found to be 243 g $Ac_2O$ per g Rh per hour. The yield of $Ac_2O$, based on the ester used, was 50.1% and the selectivity 94%.

EXAMPLE 13

2 ml (1.86 g) methyl acetate, 0.5 ml (1.14 g) methyl iodide and 1.7 g catalyst No. 9 were reacted in the autoclave with carbon monoxide at 180° C. under a CO-pressure of 20 bars. After a reaction period of 1 hour, the catalyst performance was found to be 250 g $Ac_2O$ per g Rh per hour. The yield of $Ac_2O$, based on the ester used, was 55.0% and the selectivity 95.5%.

Description of catalyst preparation

In each particular case, the catalyst carrier was activated by drying at over a period of 10 hours at 200° C. under a pressure of about 0.133 millibar. All syntheses were run in the presence of nitrogen with exclusion of oxygen and water, and all reagents were previously dried using molecular sieve 4 A.

The following abbreviations are used hereinafter
$O = C_6H_5-$
$dpe = O_2P-CH_2CH_2-PO_2$; $dpen = O_2P-CH=CH-PO_2$
$dpb = O_2P-(CH_2)_4-PO_2$
Tetraphos-1 = $O_2PCH_2CH_2POCH_2CH_2CH_2POCH_2CH_2PO_2$ Catalyst No. 1
$Al_2O_3[Rh(dpe)_2]^+Cl^-$ 3 g activated aluminum oxide balls (99% $Al_2O_3$) which had a diameter of 3 mm, an inner BET-surface area of 125 $m^2/g$ a pore volume of 0.9 ml/g were added to 150 mg (16 mg Rh) compound of the formula $[Rh(dpe)_2]Cl$ (melting point=217° C.; prepared from 1,2-bis-(diphenylphosphine)ethane and dichloroetetracarbonyldirhodium, cf. A. Sacco et al., J. Chem. Soc. (London), (1964), 3274; for preparation of $[Rh(CO)_2Cl]_2$ from $RhCl_3\cdot 3H_2O$ and CO-gas, see J. A. McCleverty et al., Inorg. Synth. 8 (1966), page 211; for preparation of $O_2PCH_2CH_2PO_2$, see W. Hewertson et al., J. Chem. Soc. (London), (1962), 1490) dissolved in 100 ml dichloromethane, under $N_2$.

The yellow suspension was heated to boiling while stirring and refluxed over a period of 12 hours after which the dichloromethane was found to have been completely decolorized. Next, the dichloromethane was removed under reduced pressure and the catalyst was dried over a period of 8 hours at 85° C. under 1.13 millibars.

Yellow pellets containing 0.44 wgt % Rh were obtained.

Catalyst No. 2
$Al_2O_3[Rh(dpe)_2]^+BF_4^-$ 3 g activated aluminum oxide balls (99% $Al_2O_3$) which had a diameter of 3 mm, an inner BET-surface area of 125 $m^2/g$ and a pore volume of 0.9 ml/g were added to 100 mg (10.4 mg Rh) compound of the formula $[Rh(dpe)_2]BF_4$ (melting point=270° C.; prepared the same way as catalyst No. 1 but with an additional anion exchange with $AgBF_4$ for increasing the performance; cf. B. R. James et al., Can. J. Chem. 57, 180 (1979) dissolved in 100 ml dichloromethane under $N_2$. The yellow suspension was heated to boiling while stirring, refluxed over a period of 12 hours after which the dichloromethane was found to have been completely decolorized. Next, the dichloromethane was removed under reduced pressure and the catalyst was dried for 8 hours at 85° C. under 1.13 millibars.

Yellow pellets containing 0.32 wgt % Rh were obtained.

Catalyst No. 3
$SiO_2[Rh(dpe)_2]^+BF_4^-$ 4 g activated silicon dioxide (98% $SiO_2$) which had a diameter of 3 mm, an inner BET-surface area of 280 $m^2/g$ and a pore volume of 0.95 ml/g was added to 193 mg (20.1 mg Rh) compound of the formula $[Rh(dpe)_2]BF_4$ dissolved in 100 ml dichloromethane under $N_2$. The yellow suspension was heated to boiling while stirring and refluxed over a period of 12 hours after which the dichloromethane was found to have been completely decolorized. Next, the dichloromethane was removed under reduced pressure and the catalyst was dried for 8 hours at 85° C. under 1.13 millibars.

Yellow pellets containing 0.47 wgt % Rh were obtained.

Catalyst No. 4
$Al_2O_3[Rh(dpb)(CO)Cl]_2$ 5.3 g activated aluminum oxide balls (99% $Al_2O_3$) which had a diameter of 3 mm, an inner BET-surface area of 125 $m^2/g$ and a pore volume of 0.9 ml/g were added to 29 mg (5.04 mg Rh) compound of the formula $[Rh(dpe)(CO)Cl]_2$ (melting point=182° C.; prepared from 1,4-bis-(diphenylphosphine)butane and dichlorotetracarbonyldirhodium; cf. A. R. Sanger, J. Chem. Soc. Dalton Trans (1977), 120) dissolved in 50 ml dichloromethane, under $N_2$. The yellow suspension was heated to boiling while stirring and refluxed over a period of 18 hours after which the dichloromethane solvent was found to have been completely decolorized. Next, the dichloromethane was removed under reduced pressure and the catalyst was dried for 8 hours at 85° C. under 1.13 millibars.

Yellow pellets containing 0.08 wgt % Rh were obtained.

Catalyst No. 5

6.3 g activated chromium/aluminum oxide cylinders (5.29 g $Al_2O_3$ + 1.01 g $Cr_2O_3$) with the dimensions of 4×4 mm and with an inner BET-surface area of 68 $m^2/g$ were added to 200 mg (20.9 mg Rh) compound of the formula $[Rh(dpe)_2]BF_4$ dissolved in 100 ml dichloromethane, under $N_2$. The green suspension was heated to boiling while stirring and refluxed over a period of 24 hours after which the dichloromethane was found to have been completely decolorized. Next, the dichloromethane was removed under reduced pressure and the catalyst was dried for 8 hours at 85° C. under 1.13 millibars. Green pellets containing 0.3 wgt % Rh were obtained.

Catalyst No. 6

$Al_2O_3[(Rh)tetraphos\ I)]^+PF_6^-$ 3.5 g activated aluminum oxide balls (99% $Al_2O_3$) which had a diameter of 3 mm, an inner BET-surface area of 125 $m^2/g$ and a pore volume of 0.9 ml/g were added to 100 ml (11 mg Rh) compound of the formula $[Rh(tetraphos-I)]^+PF_6^-$ (melting point=314° C.; prepared from $(PO_3)_3RhCl$ and tetraphos-I; cf. R. B. King et al., Inorg. Chem. Vol. 10 (1971), page 1851 et seq) dissolved in 50 ml dichloromethane, under $N_2$. The yellow suspension was heated to boiling while stirring and refluxed over a period of 16 hours after which the dichloromethane was found to have been completely decolorized. Next, the dichloromethane was removed under reduced pressure and the catalyst was dried for 8 hours at 85° C. under 1.13 millibars.

Yellow pellets containing 0.3 wgt % Rh were obtained

Catalyst No. 7

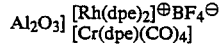

3 g activated aluminum oxide balls (99% $Al_2O_3$) which had a diameter of 3 mm, an inner BET-surface area of 125 $m^2/g$ and a pore volume of 0.9 ml/g were added to 100 mg (10.4 mg Rh) compound of the formula $[Rh(dpe)_2[BF_4$ and 100 mg (9.25 mg Cr) compound of the formula $[Cr(dpe)(CO)_4]$ (prepared as described by J. Chatt et al., J. Chem. Soc. (London) 1961, pages 4980 et seq.) dissolved in 100 ml dichloromethane, under $N_2$. The yellow suspension was heated to boiling while stirring and refluxed over a period of 12 hours after which the dichloromethane was found to have been completely decolorized. Next, the dichloromethane was removed under reduced pressure and the catalyst was dried for 8 hours at 85° C. under 1.13 millibars. Yellow pellets containing 0.31 wgt % Rh and 0.28 wgt % Cr were obtained.

Catalyst No. 8

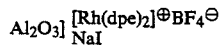

0.1 g sodium iodide dissolved in 30 ml acetone was added while stirring to 3 g activated aluminum oxide balls (99% $Al_2O_3$) which had a diameter of 3 mm, an inner BET-surface area of 125 $m^2/g$ and a pore volume of 0.9 ml/g, and the whole was heated to boiling, and refluxed over a period of 48 hours. Next, the solvent was removed and the catalyst balls were dried for 8 hours at 85° C. under 1.13 millibars.

The rhodium was applied as described hereinabove for catalyst No. 2

Yellow pellets containing 0.31 wgt % Rh and 3.12 wgt % NaI were obtained.

Catalyst No. 9

$Al_2O_3[Rh(dpen)_2]^\oplus ClO_4^\ominus$ 100 mg (10.3 mg Rh) compound of the formula $[Rh(dpen)_2]^\oplus ClO_4^\ominus$ (prepared as described by W. A. Fordyce et al., Inorg. Chem. 1982, 21, pages 1455-61) dissolved in 100 ml dichloromethane was added under $N_2$ to 3 g activated aluminum oxide balls (99% $Al_2O_3$) which had a diameter of 3 mm, an inner BET-surface area of 125 $m^2/g$ and a pore volume of 0.9 ml/g. The light yellow suspension was heated to boiling and refluxed over a period of 12 hours after which the solvent was found to have been completely decolorized. Next, the solvent was removed under reduced pressure and the catalyst was dried for 8 hours at 85° C. under 1.13 millibars. Yellowish pellets containing 0.33 wgt % Rh were obtained.

We claim:

1. A carrier-supported catalyst for making monocarboxylic anhydrides by subjecting a suitable ester or ether to a carbonylation reaction, in which the carrier has a noble metal/chelate-compound formed of a noble metal compound selected from the 8th subgroup of the Periodic System of the elements and a chelator containing organonitrogen, organophosphorus, organoarsenic or organosulfur groups applied to it, the chelator being a compound of the formula:

(a) $Y-(CH_2)_n-Y$ (b) $Y-CH=CH-Y$ (c) $O_2P-CH=CH-PO_2$ (d) $O_2As-CH=CH-AsO_2$ (e) $O_2P-CH_2-CH_2-PO-CH_2-CH_2-PO-CH_2-CH_2-PO_2$ (f) $O_2P-CH_2-CH_2-PO-CH_2-CH_2-PO_2$ (g)

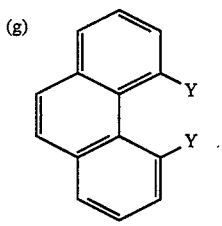

(h) P(—CH₂CH₂—PO₂)₃

(i) R¹—C[—(CH₂)ₙ—Y]₃

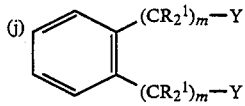

or (k) 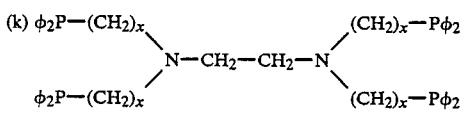

in which
O stands for C₆H₅—;
Y stands for —NR₂², an aryl group containing nitrogen, —PR₂², —AsR₂², —SR² or —SH;
R¹ stands for —H, C₁-C₅-alkyl or —C₆H₅;
R² stands for a C₁-C₆-alkyl, a C₅-C₈-cycloalkyl or —C₆H₅ or C₆H₅CH₂—;
n stands for 1 through 6;
m stands for 0 through 8, and
x stands for 1 or 2.

2. A carrier-supported catalyst as claimed in claim 1, in which R² stands for a C₁-C₆-alkyl, a C₅-C₈-cycloalkyl or —C₆H₅ or C₆H₅CH₂— substituted with halogen, methoxy-, ethoxy or a C₁-C₃-alkyl.

3. A carrier-supported catalyst as claimed in claim 1, containing an inorganic oxidic carrier or active carbon carrier.

4. A carrier-supported catalyst as claimed in claim 1, containing 0.01–50 wgt % chelate compound.

5. A carrier-supported catalyst as claimed in claim 1, in which the carrier has a non noble metal/chelate-compound formed of a non noble metal compound selected from the 6th or 8th subgroup of the Periodic System of the elements and a chelator containing organonitrogen, organophosphorus, organoarsenic or organosulfur groups additionally applied to it.

6. A carrier-supported catalyst as claimed in claim 1 containing a non noble metal compound selected from the 1st through 3rd principal groups or the 4th through 6th or 8th subgroups of the Periodic system of the elements as an additional promoter.

7. A carrier-supported catalyst as claimed in claim 6, containing altogether 0.01–50 wgt % chelate compound and non noble metal compound.

8. A carrier-supported catalyst as claimed in claim 1, having the following formula: carrier][Rh((C₆H₅)₂P—CH₂CH₂—P(C₆H₅)₂)₂]Cl.

9. A carrier-supported catalyst as claimed in claim 1, having the following formula: carrier][((C₆H₅)₂P—CH₂—CH₂—P(C₆H₅)₂)₂[BF₄.

10. A carrier-supported catalyst as claimed in claim 1, having the following formula: carrier][Rh((C₆H₅)₂P—(CH₂)₄—P(C₆H₅)₂)(CO)Cl]₂.

11. A carrier-supported catalyst as claimed in claim 1, having the following formula: carrier][Rh((C₆H₅)₂PCH₂CH₂P(C₆H₅)CH₂CH₂P(C₆H₅)CH₂CH₂P(C₆H₅)₂)]PF₆.

12. A carrier-supported catalyst as claimed in claim 5, having the following formula:

carrier] [Rh((C₆H₅)₂P—CH₂—CH₂P(C₆H₅)₂)₂]BF₄
[Cr(C₆H₅)₂P—CH₂—CH₂—P((C₆H₅)₂(CO)₄]

13. A carrier-supported catalyst as claimed in claim 6, having the following formula:

carrier] [Rh((C₆H₅)₂P—CH₂—CH₂—P(C₂H₅)₂)₂]BF₄
NaI

14. A carrier-supported catalyst as claimed in claim 1, having the following formula:

carrier] [Rh((C₆H₅)₂P—CH=CH—P(C₆H₅)₂)₂]ClO₄

15. A carrier-supported catalyst as claimed in claim 1, wherein n is a number from 1 to 4, and m is a number from 0–3.

16. A carrier-supported catalyst as claimed in claim 5, containing 0.01–50 wt.-% chelate compound.

* * * * *

UNITED STATES PATENT AND TRADEMARK OFFICE
CERTIFICATE OF CORRECTION

PATENT NO. : 4,906,415
DATED : March 6, 1990
INVENTOR(S) : Gerhard Luft and Gebhard Ritter It is certified that error appears in the above-identified patent and that said Letters Patent is hereby corrected as shown below:

The symbol "O" (for oxygen) should be replaced by the symbol "Ø" (for $C_6H_5-$) in the following places:

Column 2, formulas (c), (d), (e), (f), (h) and in line 46;

column 7, lines 61-66;

column 8, line 11;

column 10, formulas (c), (d), (e) and (f);

column 11, formula (h) and line 20.

Signed and Sealed this

Fourteenth Day of January, 1992

Attest:

HARRY F. MANBECK, JR.

*Attesting Officer*  *Commissioner of Patents and Trademarks*